United States Patent
Norman

(10) Patent No.: US 8,690,847 B2
(45) Date of Patent: Apr. 8, 2014

(54) SANITARY PROTECTION DEVICE

(76) Inventor: Charlotte Norman, Nacka (SE)

(*) Notice: Subject to any disclaimer, the term of this patent is extended or adjusted under 35 U.S.C. 154(b) by 304 days.

(21) Appl. No.: 12/936,701

(22) PCT Filed: Apr. 9, 2009

(86) PCT No.: PCT/SE2009/000185
§ 371 (c)(1),
(2), (4) Date: Nov. 8, 2010

(87) PCT Pub. No.: WO2009/126088
PCT Pub. Date: Oct. 15, 2009

(65) Prior Publication Data
US 2011/0054424 A1  Mar. 3, 2011

(30) Foreign Application Priority Data
Apr. 11, 2008  (SE) .................................. 0800822

(51) Int. Cl.
A61F 5/44  (2006.01)
(52) U.S. Cl.
USPC ............ 604/330; 604/317; 604/327; 604/328
(58) Field of Classification Search
None
See application file for complete search history.

(56) References Cited

U.S. PATENT DOCUMENTS

| 2,182,702 A | | 10/1937 | Previn |
| 2,534,900 A | | 12/1950 | Chalmers |
| 3,349,768 A | * | 10/1967 | Keane ........................... 604/347 |
| 3,528,423 A | * | 9/1970 | Lee ................................ 604/329 |
| 3,791,385 A | * | 2/1974 | Davis et al. ..................... 604/12 |
| 3,845,766 A | * | 11/1974 | Zoller ........................... 604/330 |
| 4,141,360 A | * | 2/1979 | Lasswell ....................... 604/181 |
| 4,321,921 A | * | 3/1982 | Laszczower ................... 604/35 |
| 5,718,675 A | * | 2/1998 | Leijd ............................. 604/11 |
| 6,264,638 B1 | | 7/2001 | Contente |
| 2002/0042599 A1 | * | 4/2002 | Zhao et al. .................... 604/367 |

FOREIGN PATENT DOCUMENTS

SE  363 734 B  2/1974
WO  2006/058409 A1  6/2006

OTHER PUBLICATIONS

International Search Report, dated Jul. 20, 2009, from corresponding PCT application.

* cited by examiner

Primary Examiner — Jackie Ho
Assistant Examiner — Eric Bryant
(74) Attorney, Agent, or Firm — Young & Thompson

(57) ABSTRACT

A sanitary protection device intended to be placed in the user's vagina (7). Distinguishing features of the sanitary protection device are that it includes a shell-like basic element (1), that the basic element (1) has in its height direction (H) a shape which narrows both upwards and downwards from an intermediate portion, and that the basic element (1) is provided with apertures (5) along part of its external surface.

19 Claims, 2 Drawing Sheets

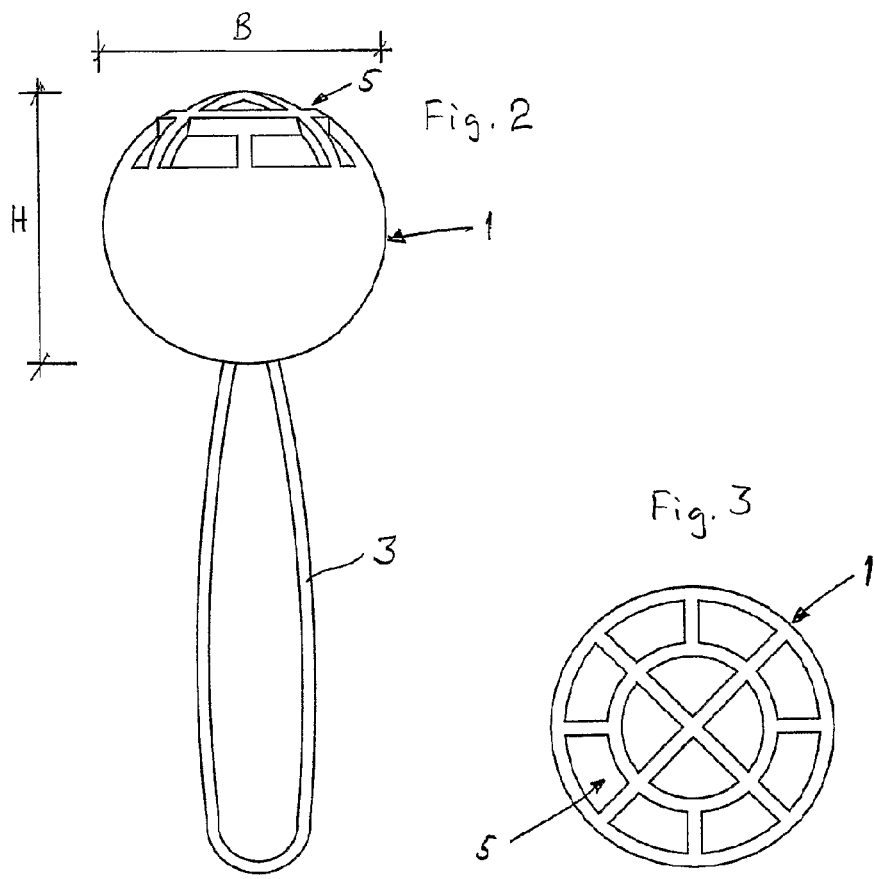
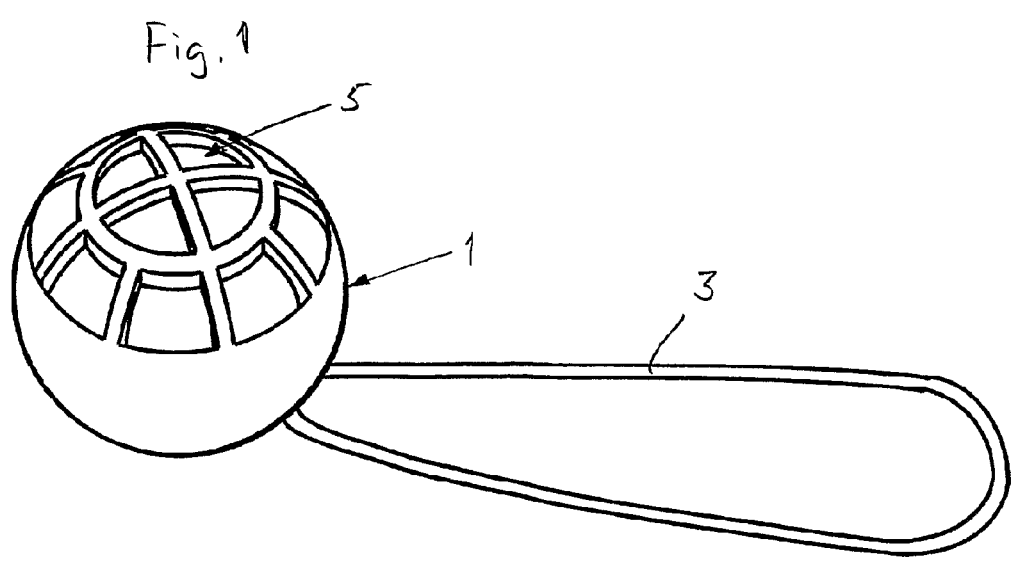

SANITARY PROTECTION DEVICE

TECHNICAL FIELD OF THE INVENTION

The present invention relates to a sanitary protection device intended to be placed in the user's vagina, which device comprises a shell-like basic element having in its height direction a shape which narrows both upwards and downwards from an intermediate portion, which basic element is provided with apertures along part of its external surface. The device is preferably intended to be used more than once.

STATE OF THE ART

A sanitary protection device known from U.S. Pat. No. 3,791,385 takes the form of an egg-shaped shell with perforations in an upper portion of the shell. An absorbent filler material intended in principle to fill the internal volume of the shell is disposed in the shell. There are good reasons for supposing that the sanitary protection device according to U.S. Pat. No. 3,791,385 is intended to be used only once. This is indicated by the fact that the parts of the shell are permanently connected to one another. This means that the filler material when full of blood is not accessible for removal of blood from it, nor for cleaning of the filler material.

A cup-shaped sanitary protection device known from SE 363 734 has annular bulges which extend round the circumference of the cup wall, preferably in a wavy line formation. In the region of the lower end of the cup there is a finger grip intended to be used when taking the device out after use.

A sanitary protection device known from U.S. Pat. No. 2,182,702 comprises a container or bag whose shape and size are such that it fills the vagina, thereby retaining the device in the vagina. The device also comprises a flange/collar that is connected to one end of the container/bag. In active position the flange/collar is intended to enclose the wearer's cervix. The other end of the container/bag has connected to it an outlet pipe provided with a plug at the far end from the container/bag. Upon removal of the plug, the blood accumulated in the container/bag can be drained off.

OBJECTS AND FEATURES OF THE INVENTION

A primary object of the present invention is to propose a sanitary protection device of the kind defined above which is of such a shape as to facilitate the application of the device in the vagina.

Another object of the present invention is that the device is intended to be used more than once.

A further object of the present invention is that the shape of the device should make it easy to place correctly in the vagina.

A still further object of the present invention is that the shape of the device should prevent leakage.

At least the primary object of the present invention is achieved by a device which has the features indicated in the attached independent claim 1. Preferred embodiments of the invention are defined in the dependent claims.

BRIEF DESCRIPTION OF THE DRAWINGS

A preferred embodiment of the invention is described below with reference to the attached drawings, in which:

FIG. 1 depicts a perspective view obliquely from above of a sanitary protection device according to the present invention;

FIG. 2 depicts a side view of the sanitary protection device according to FIG. 1;

FIG. 3 depicts a plan view of the sanitary protection device according to FIG. 1.

DETAILED DESCRIPTION OF A PREFERRED EMBODIMENT OF THE INVENTION

Figure 4:
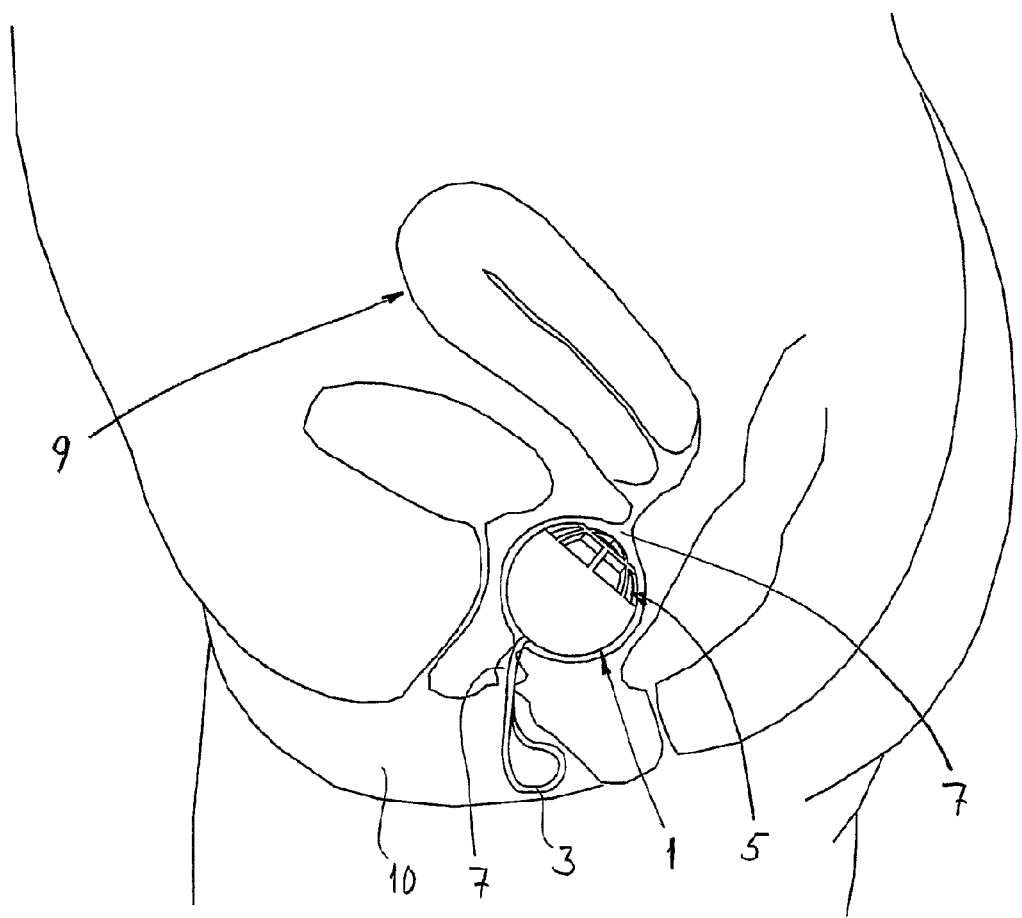
FIG. 4 depicts a schematic section through a female human body and how the sanitary protection device according to the present invention is placed therein.

The sanitary protection device depicted in FIGS. 1-3 comprises a basic element 1 which in the embodiment depicted is generally spherical. The spherical basic element 1 is shell-like, i.e. it defines an internal space which is empty. The basic element 1 is preferably made of plastic or rubber. Alternatively, the material of the basic element (1) is a decomposable material. In FIG. 2, the height direction of the basic element 1 is designated H and its width direction B. The device according to the present invention comprises also a cord 3, preferably in the form of a loop, which cord 3 is permanently fastened to the basic element 1. The cord 3 is preferably made of plastic.

As illustrated in FIGS. 1-3, the basic element 1 has apertures 5 along part of its external surface. In the embodiment depicted, the portion of the external surface of the basic element 1 which defines a dome is provided with apertures 5. This is most clearly illustrated in FIG. 2.

The shape and size of the apertures 5 formed in the basic element 1 are such that the remaining reinforcing ribs maintain the spherical shape of the basic element 1 even in the region of the apertures 5. This is primarily the case when the basic element 1 is in an unstressed state.

As most clearly illustrated in FIG. 2, the cord 3 is attached to the portion of the basic element 1 which faces away from the apertures 5. As most clearly illustrated in FIG. 2, the portion of the basic element 1 which is provided with holes has an extent in the height direction of the basic element 1 which is smaller than half the diameter of the basic element 1. This is necessary to make it possible for the basic element 1 to be fully functional as a container for accumulation of blood.

By way of non-limitative example, it may be indicated that a suitable diameter for the basic element 1 has been found to be about 40 mm.

FIG. 4 depicts a section through part of a human female body, with the genitalia depicted schematically. A sanitary protection device according to the present invention is placed in the vagina 7, which extends between the uterus 9 and the outer labia 10. The spherical shape of the basic element 1 makes it easy to introduce into the vagina 7, the basic element 1 being inserted in the vagina 7 the same distance as an ordinary tampon. In this context it should be noted that the spherical shape results in the walls of the vagina 7 abutting against the basic element 1 along only part of the external surface of the basic element 1. The basic element 1 of the sanitary protection device according to the present invention is caused to assume its operational position by orientation of the basic element 1 so that the apertures 5 face towards the cervix. This is achieved by the user taking hold of the cord and carrying out the necessary correction of the position of the basic element 1. When the basic element 1 has assumed its operational position, the cord 3 extends out from the vagina 7 and is situated between the outer labia 10.

As illustrated by FIG. 4, the vagina 7 accommodates its shape to the basic element 1, thereby effectively preventing leakage of blood via the vagina 7. The apertures 5 on the portion of the spherical basic element 1 which faces towards the cervix cause menstrual blood to pass through the apertures 5 and accumulate in the portion of the basic element 1 which is not provided with apertures. A sanitary protection device with the dimensions exemplified above can accumulate about 20 ml of blood, substantially corresponding to the amount of blood which a woman menstruates on average in 24 hours.

When it is time to remove the sanitary protection device, this is done by the user taking hold of the cord 3 and pulling the basic element 1 out from the vagina 7. The accumulated blood is poured out and the spherical basic element 1 and the cord 3 are rinsed. Thereafter the sanitary protection device can be put back in position according to FIG. 4, and the same procedure can be repeated until the menstruation has ended.
Conceivable Modifications of the Invention The embodiment described above refers to a sanitary protection device which comprises a spherical basic element 1. Within the scope of the present invention, however, it is possible to conceive of the basic element having a shape which differs somewhat from spherical. A basic concept of the present invention is that the insertion of the basic element in the vagina should be possible without discomfort for the user. In general terms, the basic element therefore needs a shape whereby only in the intermediate portion does it have its greatest diameter in the width direction B, see FIG. 2. Accordingly, the basic element narrows in the height direction H, see FIG. 2, both upwards and downwards from the intermediate portion. By way of non-limitative examples, it may be mentioned that the basic element may be egg-shaped, oval or ellipsoidal.

In this context it should also be noted that if the basic element is made of a relatively softer material, a certain deformation of the basic element may take place as it is inserted in the vagina 7, which deformation normally entails the basic element being squeezed somewhat in the width direction B in the region of its largest diameter. The deformation should of course not cause any substantial reduction of the areas of the apertures 5. Even in cases where a certain deformation of the basic element takes place in the course of applying it in the vagina 7, the apertures 5 have to be fully effective in allowing blood to pass to the interior of the basic element.

The sanitary protection device according to the present invention is primarily intended to be used more than once, i.e. the basic element 1 being taken out of the vagina 7, emptied of blood and cleaned, i.e. being normally rinsed before being reapplied in the user's vagina 7. Within the scope of the present invention, however, it is possible for the sanitary protection device according to the present invention to be intended to be used only once, i.e. the basic element being removed from the vagina 7 and emptied and the whole sanitary protection device, including the basic element 1 and the cord 3, being discarded.

The invention claimed is:

1. A sanitary protection device intended to be placed in a user's vagina (7), the sanitary protection device comprising a shell-like basic element (1) having in a height direction (H) a shape which narrows both upwards and downwards from an intermediate portion, the basic element (1) being provided with apertures (5) along part of an external surface of the basic element, wherein an internal surface of the basic element (1) defines an outermost boundary of a completely empty interior space and that the intermediate portion of the basic element (1) provided with apertures (5) has an extent in the height direction (H) which is smaller than half the a height of the basic element (1).

2. The sanitary protection device according to claim 1, wherein the basic element (1) is spherical.

3. The sanitary protection device according to claim 2, wherein the apertures (5) are disposed on a portion of the external surface of the spherical basic element (1) which defines a dome.

4. The sanitary protection device according to claim 1, wherein the basic element (1) has a means for gripping (3) on a portion that faces away from the apertures (5).

5. The sanitary protection device according to claim 4, wherein the means for gripping (3) takes a form of a cord (3).

6. The sanitary protection device according to claim 1, wherein the basic element (1) is made of rubber or plastic.

7. The sanitary protection device according to claim 1, wherein the basic element (1) is made of a decomposable material.

8. The sanitary protection device according to claim 1, wherein the basic element (1) is made of a non-reusable material.

9. The sanitary protection device according to claim 2, wherein the basic element (1) has a means for gripping (3) on a portion that faces away from the apertures (5).

10. The sanitary protection device according to claim 3, wherein the basic element (1) has a means for gripping (3) on a portion that faces away from the apertures (5).

11. The sanitary protection device according to claim 2, wherein the basic element (1) is made of rubber or plastic.

12. The sanitary protection device according to claim 2, wherein the basic element (1) is made of a decomposable material.

13. The sanitary protection device according to claim 2, characterized in that the basic element (1) is made of a non-reusable material.

14. The sanitary protection device according to claim 1, wherein all of the apertures (5) lead into the empty interior space.

15. A sanitary protection device for controlling menstrual fluid comprising:
   a hollow reservoir unit (1) with an internal surface defining an outermost boundary of an internal cavity constructed and arranged to (i) be completely empty immediately prior to insertion of the hollow reservoir unit into a user's vagina and (ii) store menstrual fluid after insertion of the hollow reservoir unit into the user's vagina, the hollow reservoir unit including:
      a first end constructed and arranged to, after insertion, face toward the user's cervix,
      a second end constructed and arranged to, after insertion, face toward the user's outer labia, and
      an intermediate portion disposed between the first end and the second end,
      wherein the hollow reservoir unit (1) narrows from the intermediate portion to the first end and from the intermediate portion to the second end,
      wherein the hollow reservoir unit defines a plurality of apertures (5) disposed on its outer surface only in an area between the first end and the intermediate region, the plurality of apertures (5) extending a distance along a height (H) of the hollow reservoir unit (1), the distance being less than half the height (H).

16. The sanitary protection device according to claim 15, further comprising:
   a cord (3) connected to the second end of the hollow reservoir unit (1), the cord being constructed and arranged to remove the hollow reservoir unit (1) from the user's vagina.

17. The sanitary protection device according to claim 15, wherein all of the plurality of apertures (5) lead into the internal cavity.

18. The sanitary protection device according to claim 1, wherein the basic element (1) is constructed and arranged to surround the empty interior space and nothing else.

19. The sanitary protection device according to claim 15, wherein the hollow reservoir unit is constructed and arranged, immediately prior to insertion of the hollow reservoir unit into a user's vagina, to surround the internal cavity and nothing else.

\* \* \* \* \*

UNITED STATES PATENT AND TRADEMARK OFFICE
CERTIFICATE OF CORRECTION

PATENT NO.        : 8,690,847 B2
APPLICATION NO.   : 12/936701
DATED             : April 8, 2014
INVENTOR(S)       : Charlotte Norman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 332 days.

Signed and Sealed this

Twenty-ninth Day of September, 2015

Michelle K. Lee
*Director of the United States Patent and Trademark Office*